United States Patent [19]

Bonnefous

[11] Patent Number: 5,103,826
[45] Date of Patent: Apr. 14, 1992

[54] DEVICE FOR MEASUREMENT AND DISPLAY OF PHYSIOLOGICAL PARAMETERS OF A BLOOD FLOW BY ULTRASONIC ECHOGRAPHY

[75] Inventor: Odile Bonnefous, Nogent sur Marne, France

[73] Assignee: U.S. Philips Corporation, New York, N.Y.

[21] Appl. No.: 619,276

[22] Filed: Nov. 28, 1990

[30] Foreign Application Priority Data

Dec. 1, 1989 [FR] France .................. 89 15900

[51] Int. Cl.⁵ .............................. A61B 8/02
[52] U.S. Cl. ................... 128/661.08; 128/661.09; 73/861.25
[58] Field of Search .............. 128/661.08, 661.09, 128/661.10; 73/861.25

[56] References Cited

U.S. PATENT DOCUMENTS

| | | | |
|---|---|---|---|
| 4,803,990 | 2/1989 | Bonnefous et al. | 128/661.08 |
| 4,840,180 | 6/1989 | Ito et al. | 128/661.08 |
| 4,853,904 | 8/1989 | Pesque | 128/661.08 |
| 5,010,528 | 4/1991 | Ohtsuki et al. | 128/661.09 |
| 5,031,628 | 7/1991 | Nakamura et al. | 128/661.09 |

*Primary Examiner*—Francis Jaworski
*Assistant Examiner*—George Manuel
*Attorney, Agent, or Firm*—William Squire

[57] ABSTRACT

A device for the measurement and display of physiological parameters of a blood flow (10), comprising a unit (300) for measuring, using ultrasonic echography, the speed V(t,z) of blood flow as a function of time t and scanning depth z. The measurement of the speed V(t,z) is independent of the frequency of the ultrasonic wave used. The device for measurment and display comprises, connected to an output of a first memory (304) for storing speed values V(t,z), a multiplexer (401) which writes, for a given instant t, the number $N_i(t)$ of measurement samples having the value $V_i$ to within $\Delta V$, $\Delta V$ being the discretization step, into a register i of a second memory (402) and a device (403) for displaying the speed as a function of time, such that the brightness at the point (Vi,t) is proportional to $N_i(t)$.

8 Claims, 1 Drawing Sheet

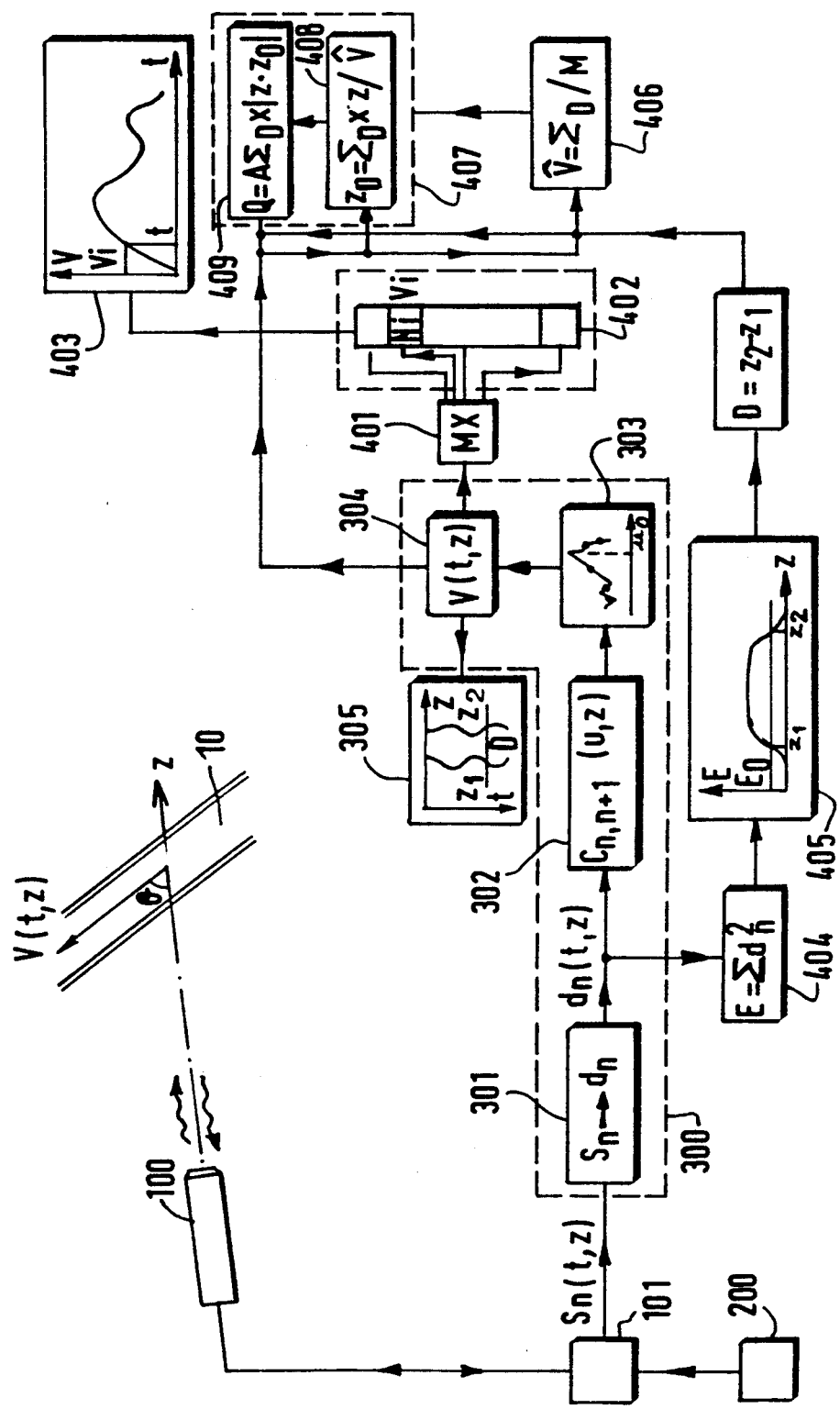

DEVICE FOR MEASUREMENT AND DISPLAY OF PHYSIOLOGICAL PARAMETERS OF A BLOOD FLOW BY ULTRASONIC ECHOGRAPHY

BACKGROUND OF THE INVENTION

The invention relates to a device for the measurement and display of physiological parameters of a blood flow, comprising a unit or measuring, using ultrasonic echography, the speed $V(t,Z)$ of said flow as a function of time t and scanning depth z.

The invention can be particularly attractively used in the general field of echographic scanning of blood flows in vessels, and notably for the measurement and display of physiological parameters characterizing said blood flows for diagnostic purposes.

Clinical examination of blood flows by ultrasonic echography is carried out at present using apparatus based on the Doppler effect which takes into account the frequency difference, referred to as the Doppler frequency $f_D$, between the wave emitted by a Piezoelectric transducer and the wave received after interaction with the relevant flow. The speed V of the blood flow is linked to $f_D$ as:

$$f_D = 2(V/C)f_E\cos\theta \quad (1)$$

where $f_E$ is the frequency of the emitted ultrasonic wave, $\theta$ is the angle enclosed by the ultrasonic beam with respect to the flow direction, and C is the propagation speed of sound.

The known Doppler devices notably offer access to interesting parameters, such as the speed spectrogram giving the distribution of the flow speed V as a function of the time t. However, the result obtained lacks a given precision which is inherent of the principle of the method itself and which is caused by the fact that the frequency $f_E$ emitted by the piezoelectric transducer exhibits a given spread which has an effect on the speed V via the above relation (1). Among the devices capable of performing a speed measurement independently of the ultrasonic frequency there are those which operate according to the time correlation principle described in European Patent Application No. 0 225 667 which corresponds to U.S. Pat. No. 4,803,990 whose unit for measuring the flow speed comprises an intercorrelation circuit which supplies correlation function values on the basis of two successive echoes, and a multiplexing/interpolation circuit which supplies an estimate of the speed $V(t, z)$ on the basis of the correlation function values.

SUMMARY OF THE INVENTION

The technical problem to be solved by the invention, therefore, is to provide a device for the measurement and display of physiological parameters of a blood flow of the kind set forth which enables a more exact spectrogram of the speeds to be obtained and which also enables determination of supplementary physiological parameters.

A solution to the technical problem in accordance with an embodiment of the invention is in that, the measurement of the speed $V(t,z)$ being independent of the frequency of the ultrasonic wave used, the device for measurement and display comprises, connected to an output of a memory for storing values of the speed $v(t,z)$, a multiplexer which writes, for a given instant t, the number $N_i(t)$ of measurement samples having the value $V_i$ to within $\Delta V$, $\Delta V$ being the discretization step, into a register i of a memory, and a device for displaying the speed as a function of time, such that the brightness at the point $(v_{i,t})$ is proportional to $N_i(t)$.

The precision obtained as regards the measurement of the flow speed enables, in addition to the display of the blood flow in, for example, the M-mode and the representation of the speed spectrogram, calculation of other physiological parameters thus far inaccessible by conventional Doppler systems because of their poor resolution as a function of depth. Among the parameters which can be determined according to the present invention, there are the flow diameter $D(t)$, the mean speed $V(t)$, and the rate $Q(t)$ of the blood flow. The technical means for calculating the various parameters will be described in detail hereinafter with reference to the accompanying drawing.

BRIEF DESCRIPTION OF THE DRAWING

The scale figure shows the diagram of a device for measurement and display in accordance with an embodiment of the invention.

DESCRIPTION OF THE PREFERRED EMBODIMENT

The diagram shows a device for the measurement and display of physiological parameters of a blood flow 10. The device comprises a piezoelectric transducer 100 which may be, for example a multi-element array. A transmitter stage 200, connected to the transducer 100, forms an ultrasonic scanning beam and a measuring stage 300 processes the echographic signals returned to the transducer 100 in order to supply an estimate of the flow speed $V(t,z)$ as a function of the time t and the scanning depth z.

The transmitter stage 200 comprises a conventional sequencer which is composed of an oscillator and a frequency divider which controls, at the recurrent frequency 1/T chosen, a generator whose electric excitation signals are applied to the transducer 100 which converts these signals into periodic trains of ultrasonic pulse signals. A separator 101 for the transmitter stage 200 and the measuring stage 300 is inserted between the transducer 100 and stages 200, 300 and Prevents overloading of the measuring circuits by the transmitted signals.

The stage 300 for measuring the speed $V(t,z)$ comprises a fixed-echo elimination device 301 for example at two points, which supplies, on the basis of the signal $S_n(t,z)$ received, a signal $d_n(t, z)$ wherefrom the fixed components due to the specular refections from the walls of the blood vessel examined have been removed. The signal $d_n(t,z)$ supplied by the fixed-echo elimination device 301 is subsequently processed according to the intercorrelation method described in European Patent Application No. 0 225 667 which utilizes the fact that the ultrasonic signals returned by a moving target are linked by the following equation:

$$d_{n+1}(t) = d_n(t-\tau)$$

which means that the signal n+1 is a replica of the preceding signal n, except for a time shift $\tau$. The latter represents the additional time necessary for the ultrasonic wave to travel the path transducer-target-transducer transducer from one excitation to another. In other words:

$$\tau = 2VT/C$$

where V is the speed of the target and C is the speed of sound. It appears that measurement of $\tau$ enables measurement of the speed V.

The intercorrelation function between $d_n(t)$ and $d_{m+1}(t)$, defined by:

$$C_{n,n+1}(to,u) = \int_{to}^{to+W} d_{n+1}(t+u)d_n(t)dt$$

verifies that:

$$C_{n,n+1}(to,u) = C_{n,n}(to,u-\tau)$$

The time to is linked to the scanning depth z as $t0 = 2z/C$, and W is the width of the integration window.

The function $C_{nn}(to,u)$ is an autocorrelation function and hence is maximum for $u=o$. Thus, a measure of the time shift $\tau$, and hence of the speed V, can be obtained by searching for which parameter u the function $C_{n,n+1}(to,u)$ is maximum. Therefore, the intercorrelation function is sampled, using a sampling step $\Delta t$, between $u_{min} = -I\Delta t$ and $u_{max} = I\Delta t$ in steps of 1 in order to obtain $2I+1$ correlation function values. The maximum value of these $2I+1$ values corresponding to $u = uo$ enables measurement of $\tau$ by using the equality $\tau = uo$. The calculation of the correlation functions is performed by the intercorrelation circuit 302 shown in FIG. 1.

In order to remove the errors inherent of the sampling in the determination of the maximum of the correlation function, use can be made of a multiplexing/interpolation circuit 303 which supplies, on the basis of correlation function values, a more exact estimate of the speed and the value of the corresponding correlation peak. European Patent Application No. 0 225 667 describes an example of this type of processing of the echographic signal where the correlation between two signals is a so-called "1-bit" correlation in a sense that the signals $d_{n+1}$ and $d_n$ previously used are reduced to the sign of the ultrasonic signal. It is known that the peak of the correlation function is then shaped as an isosceles triangle. Knowledge of this shape enables complete reconstruction, on the basis of the highest point and its two neighbors, of the correlation peak by linear interpolation, and hence exact determination of the location of uo.

As opposed to the traditional Doppler speed measuring devices, the flow speed V(t,z) thus determined offers the advantage that it is insusceptible to the frequency spread of the ultrasonic wave used, enabling a more complete use of the results.

The values found for the speed V(t,z) are stored in a memory 304 for later processing. Using notably known display means, an image of the flow being studied can be displayed on a first screen 305 in the so-called "M-mode" representation of the evolution in the course of time of the speed profile in the vessel. The encoding of the speed is that used in CFM (Color Flow Mapping) systems: for example, the red code is a displacement direction, the blue code is the opposite direction, and the intensity of the speed is encoded through the intensity of the color.

Another particularly important operation for the user is the formation of an exact speed spectrogram. To this end, the device for measurement and display comprises, connected to the output of the memory 304, a multiplexer 401 which writes, for a given instant t, the number $N_i(t)$ of measurement samples having the value $V_i$ to within $\Delta V$, $\Delta V$ being the discretization step, into a register i of a memory 402, and a device 403 for displaying the speed as a function of time, such that the brightness at the point (Vi,t) is proportional to $N_i(t)$.

Other physiological parameters characterizing the flow can be calculated. The first is the diameter D(t) of the flow; for this measurement use is made of a circuit 404 which is connected to the output of the fixed-echo elimination device 301 and which calculates the local energy $$E(t,z) = \sum_n d_n^2(t,z),$$

and a circuit 405 for calculating the flow diameter $D(t) = z_2(t) - z_1(t)$ which is formed by an adjustable threshold detector for the value Eo, $z_1(t)$ and $z_2(t)$ being defined by $E(t,z_1(t)) = E(t, z_2(t)) = Eo$.

The flow diameter D(t) being known at each instant t, the mean speed $\hat{V}(t)$ of the blood flow can be measured, utilizing a circuit 406 which is formed by an adder which supplies $\Sigma_D V(t,z)$ and a divider-by-M, M being the number of samples of the speed V(t,z) used for the segment $[z_1,z_2]$.

Moreover, the rate Q(t) can be measured by means of a circuit 407 which comprises a circuit 408 for calculating the center of gravity $z_o(t) = \Sigma_D V(t,z)z/\hat{V}(t)$, formed by an adder supplying $\Sigma_D V(t,z)z$ and a divider-by-the-mean-speed $\hat{V}(t)$ calculated by the circuit 406, and an adder 401 which supplies $\Sigma_D V(t,z)|z-z_o|$, followed by a multiplier by the constant $A = \pi\cos\theta/\sin^2\theta$, where $\theta$ is the angle of the flow with respect to the ultrasonic beam.

What is claimed is:

1. A device for the measurement and display of physiological parameters of a blood flow comprising:
   means for measuring and sampling and, using ultrasonic echography, the speed V(t,z) of said flow as a function of time t and scanning depth z, the measurement of the speed V(t,Z) being independent of the frequency of the ultrasonic wave used;
   first memory means for storing the values of the measured speed;
   second memory means including a register i;
   multiplexing means coupled to said first and second memory means for writing from the first memory means, for a given instant t, a number $N_i(t)$ of measurement samples having a value $V_i$ within $\Delta V$, $\Delta V$ being a discretization step, into register i of said second memory means; and
   means coupled to said second memory means for displaying the speed as a function of time, such that the brightness at the point (vi,t) is proportional to $N_i(t)$.

2. A device for measurement and display as claimed in claim 1 including means for calculating local energy E(t,z) and means for calculating the flow diameter $D(t) = z_2(t) - z_1(t)$ including a threshold detector for the value Eo, $z_2(t)$ and $z_1(t)$ being defined by $E(t,z_1(t)) = E(t,z_2(t)) = Eo$.

3. A device for measurement and display as claimed in claim 2 including means for calculating the mean speed V(t) comprising an adder which supplies $\Sigma_D V(t,z)$ and a divider-by-M, M being the number of measurement samples in the segment $[z_1, z_2]$.

4. A device for measurement and display as claimed in claim 3 including means for calculating a flow rate Q(t) of said blood, comprising means for calculating the center of gravity zo(t) of the flow, formed by a first adder means for providing $\Sigma_D V(t, z)z$ and a divider means for dividing by the mean speed V(t), and a second adder means for supplying $\Sigma_D V(t,z)$ z-zo, connected to a multiplier for multiplying by the constant $A = \pi \cos^2\theta / \sin^2 \theta$, $\theta$ being an angle of the flow with respect to an ultrasonic beam.

5. A device for measurement and display as claimed in claim 4 wherein the means for measuring sampling the flow speed comprises intercorrelation means which supplies correlation function values on the basis of two received successive echoes, and means for multiplexing/interpolation which supplies in response to said intercorrelation means an estimate of the speed V(t,z) on the basis of said correlation function values.

6. A device for measurement and display as claimed in claim 3 wherein the means for measuring sampling the flow speed comprises intercorrelation means which supplies correlation function values on the basis of two received successive echoes, and means for multiplexing/interpolation which supplies in response to said intercorrelation means an estimate of the speed V(t,z) on the basis of said correlation function values.

7. A device for measurement and display as claimed in claim 2 wherein the means for measuring and sampling the flow speed comprises intercorrelation means which supplies correlation function values on the basis of two received successive echoes, and means for multiplexing/interpolation which supplies in response to said intercorrelation means an estimate of the speed V(t,z) on the basis of said correlation function values.

8. A device for measurement and display as claimed in claim 7 wherein the means for measuring the flow speed comprises intercorrelation means which supplies correlation function values on the basis of two received successive echoes, and means for multiplexing/interpolation which supplies in response to said intercorrelation means an estimate of the speed V(t,z) on the basis of said correlation values.

* * * * *